United States Patent
Mori et al.

[11] Patent Number: 6,081,607
[45] Date of Patent: Jun. 27, 2000

[54] ANIMAL BODY IDENTIFYING DEVICE AND BODY IDENTIFYING SYSTEM

[75] Inventors: Toru Mori; Yuji Kuno; Osamu Yamakita; Mitsuyoshi Tsukada, all of Tokyo, Japan

[73] Assignee: Oki Electric Industry Co., Tokyo, Japan

[21] Appl. No.: 08/772,720

[22] Filed: Dec. 23, 1996

[30] Foreign Application Priority Data

Jul. 25, 1996 [JP] Japan ................................... 8-196397

[51] Int. Cl.⁷ ........................................... G06K 9/00
[52] U.S. Cl. ..................... 382/110; 382/117; 340/825.34; 351/206
[58] Field of Search ................................... 382/114, 115, 382/113, 125, 110, 100; 351/211, 206; 348/77, 78; 340/573, 825.3, 825.34, 146

[56] References Cited

U.S. PATENT DOCUMENTS

| | | | |
|---|---|---|---|
| 4,641,349 | 2/1987 | Flom et al. | 382/115 |
| 4,993,068 | 2/1991 | Plosenka et al. | 380/201 |
| 5,016,282 | 5/1991 | Tomono et al. | 382/2 |
| 5,291,560 | 3/1994 | Daugman | 382/115 |
| 5,572,596 | 11/1996 | Wildes et al. | 382/117 |

FOREIGN PATENT DOCUMENTS

| | | |
|---|---|---|
| WO 86/05018 | 8/1986 | WIPO . |
| WO 90/03070 | 3/1990 | WIPO . |
| WO 94/25857 | 11/1994 | WIPO . |

OTHER PUBLICATIONS

"Sleuthing by Computer", 8045 IEEE Spectrum, vol. 20 (1983) Jul., No. 7, New York, USA.

*Primary Examiner*—Bhavesh Mehta
*Attorney, Agent, or Firm*—Venable; Robert J. Frank; Catherine M. Voorhees

[57] ABSTRACT

An animal body identifying device of the present invention includes a camera for photographing an eye of an animal, a body data capturer for capturing body data for the photographed animal from an image photographed by the camera, a body data registry for pre-storing a plurality of body data and a body data collator for correlating body data stored in the body data registry with body data captured by the body data capturer and identifying whether or not the photographed animal is a registered animal. An animal body identifying system of the present invention includes a body data capturing device for photographing an eye of an animal and capturing body data for the animal and a body data comparing device for collating body data obtained from the body data capturing device with pre-registered body data and determining whether or not the photographed animal is a registered animal.

14 Claims, 13 Drawing Sheets

PEDIGREE REGISTRATION DOCUMENT

NATALIE KING MACEY   PEDIGREE REGISTRATION DATE
                                    11TH JULY, 1994
                     DATE
                     11TH, JULY, 1994

BLOOD REGISTRATION  BORN 1993    NUMBER 765
TYPE                THOROUGHBRED   MALE
CHARACTERISTICS  DAIRYUSEI BIRYO OJIRO, UMOKU NE,
                 HACCHU

ADDRESS OF BREEDER: OAZA, HIDAKA, HOKKAIDO
NAME:               KASUGA ICHIRO
BREEDING PLACE: FOOT OF MT. URAGA, HOKKAIDO
FATHER:
        THOROUGHBRED   MATT DENNIS
MOTHER:
        THOROUGHBRED   PEGGY LEE

JURIDICINAL FOUNDATION   JAPAN RACEHORSE
                         REGISTRY

FIG. 16

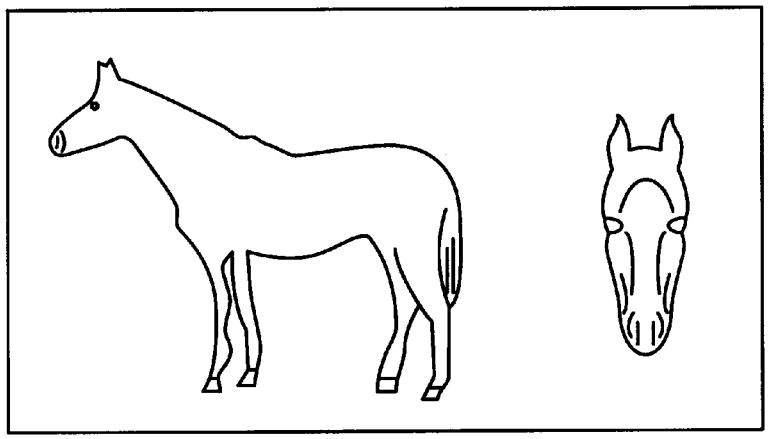

FIG. 17

ANIMAL BODY IDENTIFYING DEVICE AND BODY IDENTIFYING SYSTEM

BACKGROUND OF THE INVENTION

1. Field of the Invention

The present invention relates to a device and system for identifying animal bodies, and more particularly relates to a device and system for identifying bodies employing, for example, data for irises of eyes showing body characteristics necessary in the management of bodies of animals such as horses and cattle.

2. Description of the Related Art

Racehorse body identification occurring at horse racecourses, auction houses and breeding stock farms has conventionally mainly been carried out based on pedigree certificate supervisory facilities. Methods using hair color, leg marking characteristics, head flashes, hair curl and blood type are currently used throughout the world as methods for identifying horses at racecourses. The use of brand-irons and tattoos then makes these methods complete. However, when carrying out identification using hair color, leg marking characteristics, head flashes and hair curl, there are a lot of horses that have few characteristics or that have the same characteristics and the specifying of a horse is therefore often incomplete. Further, in addition to the erasure and falsification of the brand-irons and tattoos, there is also the problem of the pain and localized festering the animal receives, with improvements also being desirable from the point of view of the welfare of the animals. Moreover, identifying bodies using the blood type is accurate, but not only does this process take a long time until a decision is made, it is also expensive.

In the case of body identification of cattle, methods using identification, nameplates such as neck rings and ear tags, brand-irons and tattoos etc. are carried out. However, there is also the danger of the identification nameplate becoming damaged, lost or stolen, as well as the same problems with identifications using brand-irons or tattoos as encountered in the identification of horses. In particular, in the case of falsification, even if it is apparent that a falsification has been made, it is difficult to verify where the original belongs.

In recent years, identifying technology utilizing microchips (hereinafter abbreviated to MC) has become prominent as a method of identifying animal bodies (For example, refer (in particular) to The Japan Racing Association racehorse general research institute issue of "horse studies" Vol. 25(9) page 318 to 329). Here, there is a method where a chip built into a micro-integrated circuit enclosed in a glass tube is embedded into the living body of an animal using a syringe, etc., the area at which the circuit is embedded is looked into using a non-contact sensor and an output signal is then taken as body identifying information.

However, identifying methods employing MCs have a large number of problems concerning the operativity of the embedding in the animal, localized reactions such as pain, swelling, aches and festering inflicted on the horse at the time of embedding, hindrance to the movement of the horse, along with clinical disorders, movement of the MC within the horse body, operativity of the sensor, changes and instability in the sensitivity of the sensor, and reliability etc. As there is a great deal of resistance from people concerned with animals to the adoption of MC methods from the point of view of the welfare of the animals, it would be preferable if an identifying method could be found to replace MC identifying methods.

In MC identification methods, there is the possibility that a registration microchip embedded within the living body of the animal will be taken out and embedded into another animal. In the case of this illegal act, there is then the possibility of another animal being mistakenly identified as the correct animal.

SUMMARY OF THE INVENTION

It is therefore an object of the present invention to provide an identifying device for carrying out animal identification that does not cause animals to suffer from illness or pain.

It is a further object of the present invention to provide an animal identifying device for carrying out animal identification device that does not hinder the functioning of animals.

It is another object of the present invention to provide an animal identifying device for identifying animals in a stable and reliable manner.

It is a still further object of the present invention to provide a body identifying system for identifying animal bodies in a simple manner without the necessity of setting aside a special area for carrying out identification.

It is a yet further object of the present invention to provide a body identifying system where the work involved and clerical procedures concerning animal identification are greatly simplified.

An animal body identifying device of the present invention is therefore provided with a camera for photographing an eye of an animal, a body data capturer for capturing body data including iris or granula iridica data for the photographed animal from an image photographed by the camera, a body data registry for pre-storing a plurality of body data including registered iris or granula iridica data and a body data collator or correlator for correlating body data stored in the body data registry and body data captured by the body data capturer and identifying whether or not the photographed animal is a registered animal. Here, the body data can include iris data.

According to the animal body identifying device of the present invention having the above configuration, an eye of an animal is first photographed using a camera and the body data capturer captures body data including iris granule or granula iridica data for the photographed animal from the photographed image. By photographing using a camera in this way, animals are not subjected to illness or pain and there is no fear of the bodies of animals being affected in any way. There is also no chance of a different animal being mistakenly identified as a particular animal. On the other hand, body data including a plurality of iris granule or granula iridica data is already registered at the body data registry. The captured body data and the registered body data is then compared at the body data collator or correlator and an identification is made as to whether or not the animal is a registered animal.

The animal body identifying system of the present invention is provided with a body data capturing device for photographing an eye of an animal and capturing body data including iris granule or granula iridica data of the animal and a body data collating or correlating device, connected to the body data capturing device, for correllating body data obtained from the body data capturing device and body data including pre-registered iris granule or granula iridica data and determining whether or not the photographed animal is a registered animal.

According to the body identifying system of the above configuration, animal body data is captured by the body data capturing device and this body data is compared with the body data registered at the body data collating or correlating device so as to perform animal identification.

BRIEF DESCRIPTION OF THE DRAWINGS

FIG. 16 is a view illustrating a pedigree registration certificate;

FIG. 17 is a photograph showing characteristics and hair color of a horse;

DESCRIPTION OF THE PREFERRED EMBODIMENTS

The following is a description of the embodiments of the present invention based on the drawings, with elements common to each of the drawings being given the same numerals.

First Embodiment

Figure 1:
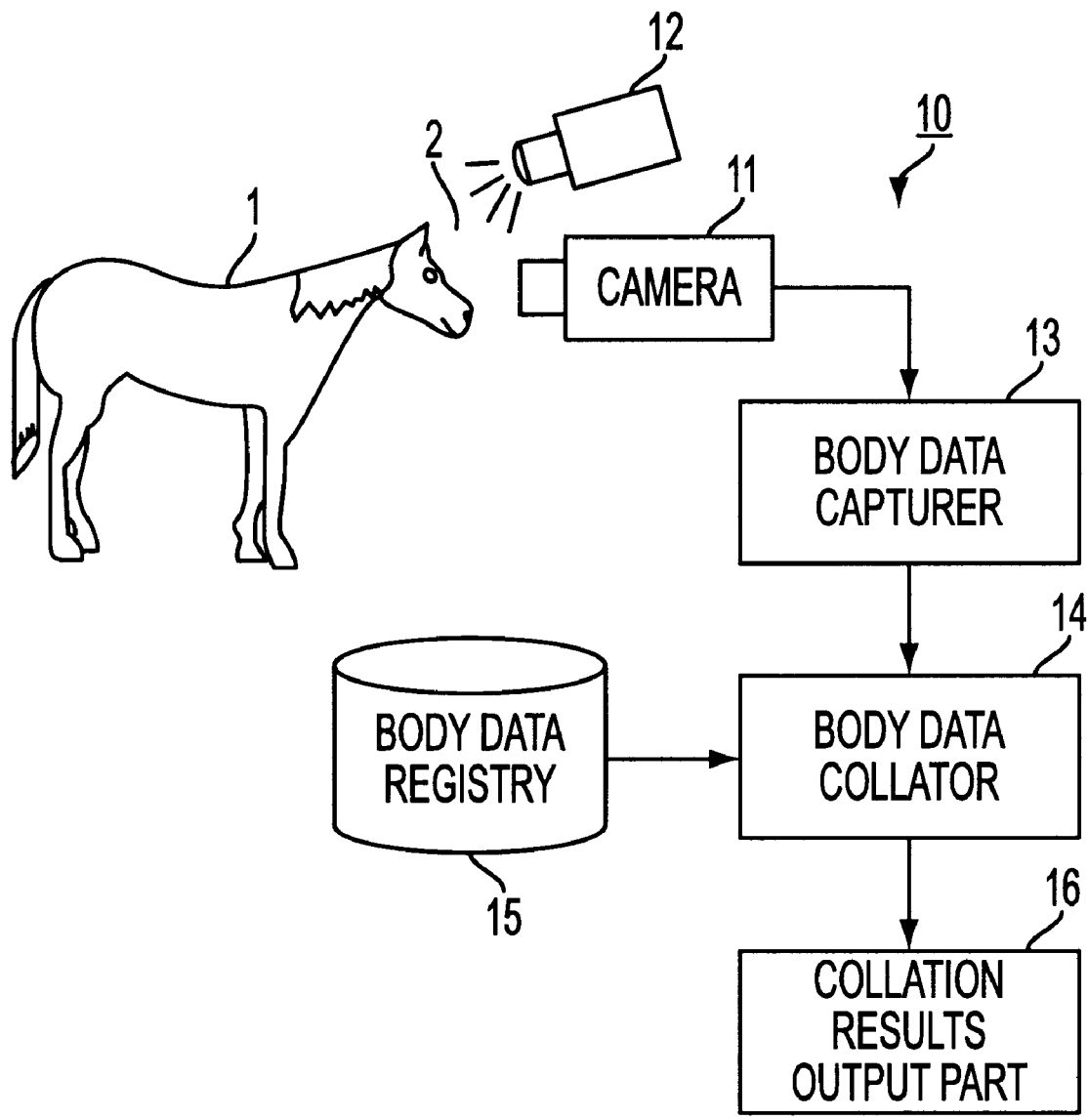
FIG. 1 is a structural view showing an animal body identifying device of a first embodiment.
Figure 2:
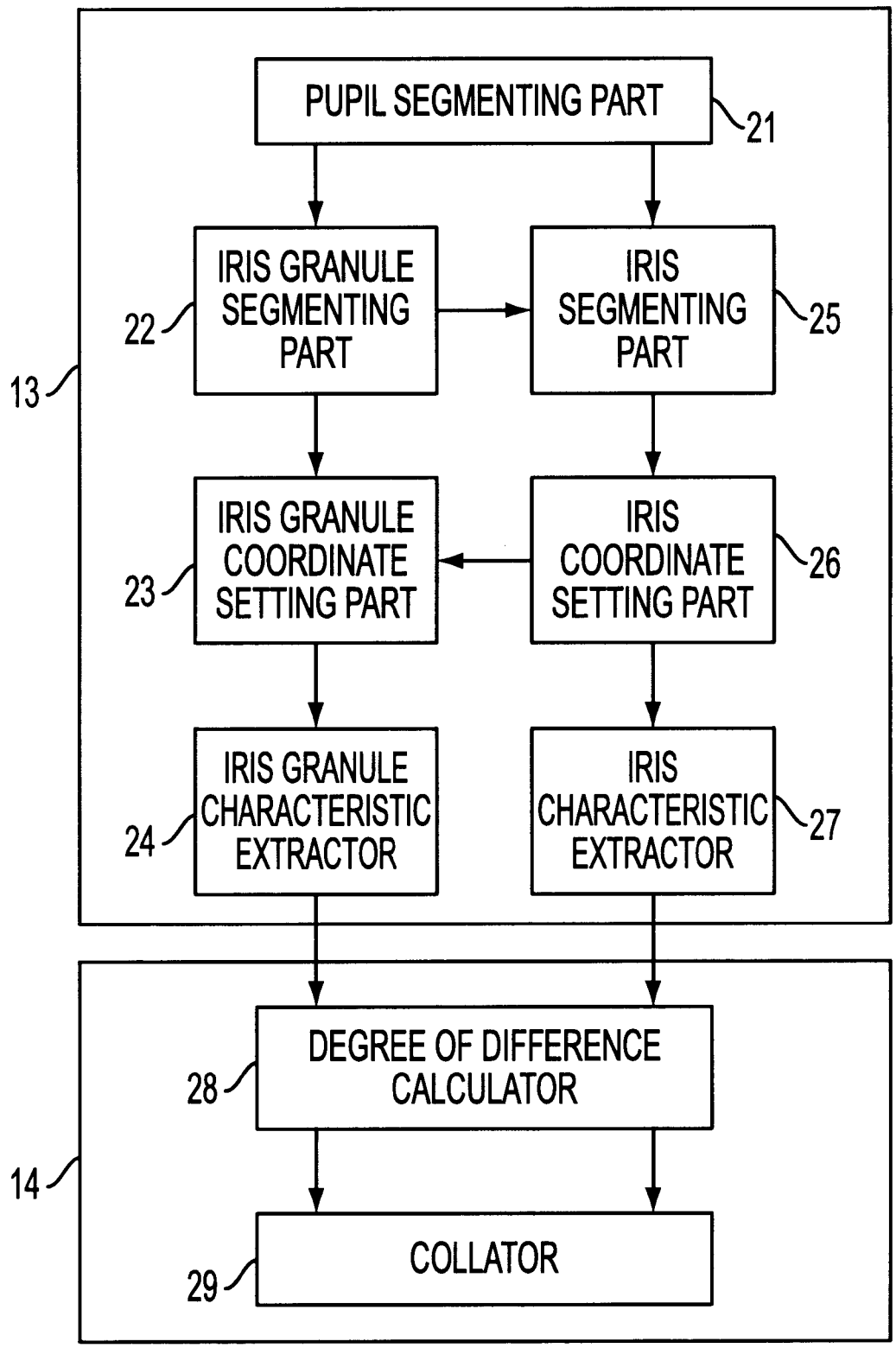
FIG. 2 is a block diagram showing the essential parts of the first embodiment.
Figure 3:
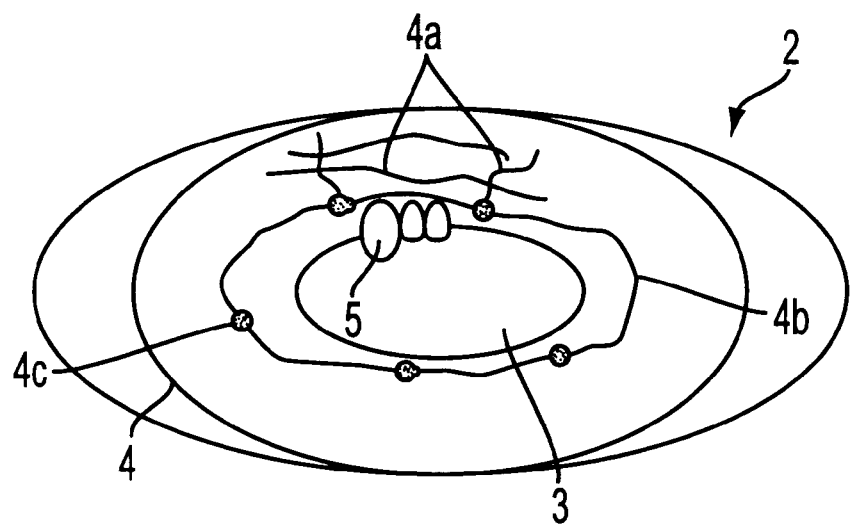
FIG. 3 is a view illustrating an eye of a horse.

The object of a first embodiment of the present invention is an animal body identifying device, with the example of a horse being taken as the animal. Here, FIG. 1 is a structural view showing the animal body identification device of the first embodiment, FIG. 2 is a block diagram showing the essential parts of the first embodiment and FIG. 3 is a view illustrating an eye of a horse. The present invention is for carrying out body identification based on data for the irises and the granulae iridica of horses. A description will first be given of the irises and granulae iridica of horses.

In FIG. 3, the eye 2 of the horse 1 is an approximately elliptical shape, with a pupil 3 at the center, surrounded by an iris 4. The pupil 3 is an approximately elliptical shaped portion through which light from outside passes, with this light then reaching a retina at the back of the pupil 3. The iris 4 is an approximately elliptical band shape surrounding the pupil 3 for adjusting the amount of light passing through the pupil 3. This iris 4 portrays the various characteristics of the body. Namely, wrinkle walls 4a are approximately elliptical band-shaped wrinkles extending in the circumferential and radial directions of the iris 4. A dividing ring 4b is a boundary dividing the iris 4 into approximately elliptical shapes. Further, a hole 4c is a depression existing within the region of the iris 4. These characteristics are distributed so as to be different for every body (horse), and an iris image particular to a body can then be formed when the body is photographed.

Iris granules or granulae iridica 5 exist at the boundary portion (upper part) of the iris 4 and the pupil 3. The iris granules 5 have a function for adjusting the amount of light passing through the pupil 3 in the same way as the iris 4, and are formed in a row as semi-spherical protruding granules. There is also some minute unevenness on the surface of the iris granules 5. The shape, surface unevenness and positioning of the iris granules is different for each body, and an image characterizing a body can be formed when the iris granules are photographed with a camera.

In FIG. 1, a body identifying device 10 of the first embodiment comprises a camera 11, a light 12, a body data capturer 13, a body data correlator 14, a body data registry 15 and a correlation results output section 16. The camera 11 puts an image of the eye 2 of a horse 1 into the form of a signal. The eye 2 of the horse 1 is illuminated using the light 12 in order to give the image of the eye 2 of the horse 1 improved contrast. The light 12 employs a light source such as red or almost red light of a wavelength that is difficult for the animal to sense so that the horse 1 that is the object does not become dazzled and move it's head. The body data capturer 13 extracts the characteristics of the iris pattern and the pattern of the iris granules or granulae iridica from the image signal obtained by the camera 11 as body data for the horse 1. The body data correlator 14 correlates iris data and iris granule data of bodies (horses) stored in the body data registry 15 and the iris patterns and iris granule or granula iridica patterns extracted by the body data capturer 13 and identifies whether or not the horse that is the object of examination is the corresponding horse. The correlation results output section 16 is for outputting the correlation results of the body data correlator 14 and can be, for example, a display device.

FIG. 2 is a view showing a specific configuration of the body data capturer 13 and the body data collator 14. In FIG. 2, the body data capturer 13 comprises a pupil segmenting part 21, an iris granule segmenting part 22, an iris granule coordinate setting part 23, an iris granule characteristic extractor 24, an iris segmenting part 25, an iris coordinate setting part 26 and an iris characteristic extractor 27. The pupil segmenting part 21 extracts regions of the pupil 3 from an image obtained at the camera 11. The iris granule segmenting part 22 extracts the region of the iris granules or granulae iridica 5 shown in FIG. 3. The iris granule coordinate setting part 23 sets coordinates for evaluating the characteristics for the extracted region of the iris granules 5. The iris granule characteristic extractor 24 extracts characteristic amounts peculiar to the body. The iris segmenting part 25 extracts the rings of regions of the iris 4 shown in FIG. 3. The iris coordinate setting part 26 sets coordinates for evaluating the characteristics of the extracted region of the iris 4. Further, the iris characteristic extractor 27 extracts characteristics peculiar to the body.

A degree of difference calculator 28 and a comparator 29 are also provided at the body data correlator 14. The degree of difference calculator 28 calculates the degree of difference between a body descriptor obtained by the iris granule characteristic extractor 24 of the body data capturer 13 and a body descriptor stored in the body data registry 15. The comparator 29 distinguishes and collates or compares the body currently being photographed based on the degree of difference obtained at the degree of difference calculator 28. For example, the name of the item corresponding to the body having the smallest degree of error within all of the descriptors for the body data registry 15 is then outputted.

Next, the operation of the first embodiment will be described in accordance with FIG. 4 to FIG. 9. FIG. 4 to FIG. 9 are views illustrating the operation of the first embodiment.

Figure 4:
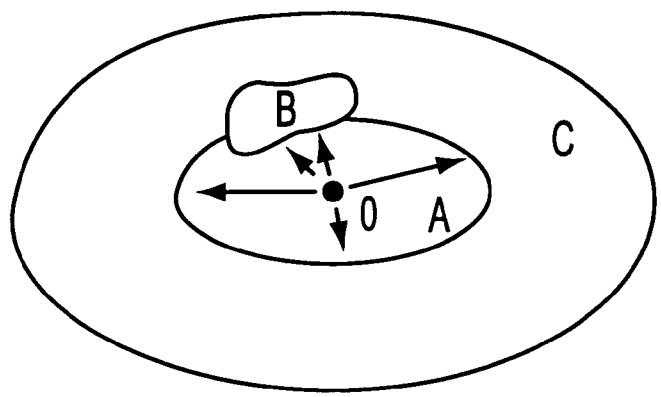
FIG. 4 is a view illustrating a pupil region segmenting process.

First, the eye 2 of the horse 1 is photographed by the camera 11, with an image signal obtained by this photographing being sent to the body data capturer 13. A pupil region is then extracted from the image photographed by the camera 11 at the pupil segmenting part 21 of the body data capturer 13. FIG. 4 shows the segmenting method for this case. In FIG. 4, region A shows the region of the pupil 3, region B shows the region of the iris granules or granulae iridica 5 and region C shows the region of the iris 4. The eye 2 is illuminated by the light 12 while the eye 2 is photographed by the camera 11 but the pupil region A reflects little light compared to the iris region C and the iris granules region B. This means that this region of the image is of a low-density and uniform. If a density change detection process represented by, for example, a Sobel operator is then carried out, the value of the density change will become approximately zero because the density of the pupil region A is uniform. The density change is therefore small and the pupil region A can be extracted by extracting a region having a surface area within the range of predetermined threshold values.

However, more detailed searches are carried out and the boundary of the pupil region A or more specifically, the outline is extracted because there are cases where the boundary of the pupil region A and the iris region C and iris granule region B cannot be extracted properly due to noise, etc. For example, when the effective center of the pupil region A roughly extracted in the process is taken to be 0, a position for which the density change largely is searched for in an outward direction taking the point 0 as the center (the directions of the arrows shown in FIG. 4). The position where the change in density becomes large is viewed as the outline of the pupil region A and a sequence of points is extracted for the outline. The method for extracting the pupil region A is by no means limited to the method, and other methods are also suitable. For example, it would also be possible to directly extract the regions for the pupil, iris and iris granules from the image shown in FIG. 4 based on texture information.

Figure 5:
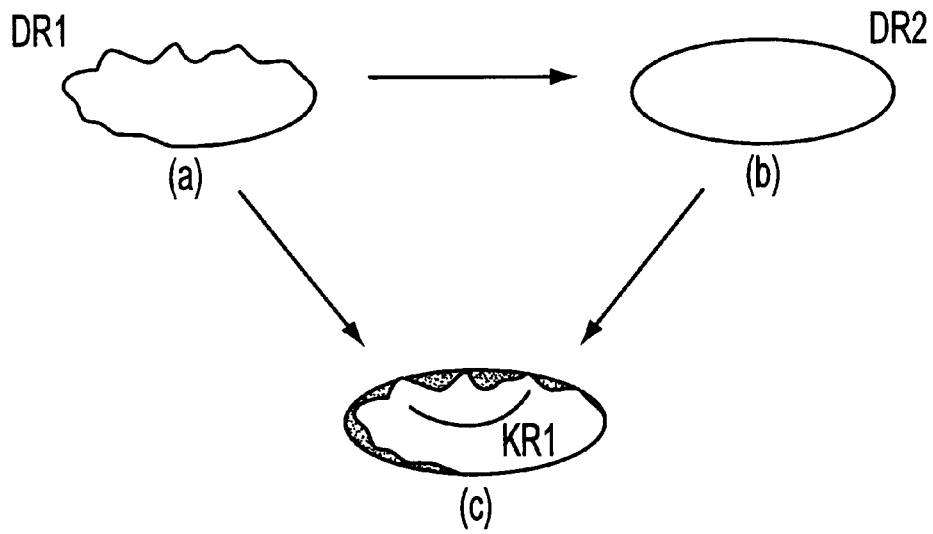
FIG. 5 is a view illustrating an iris granule region segmenting process.

When the outline of the pupil region A is extracted at the pupil segmenting part 21, the iris granule region B is then extracted at the iris granule segmenting part 22. A description will be given with regards to this extraction using FIG. 5 and FIG. 6. A closed curved line DR1 shown in FIG. 5(a) is a sequence of points showing the line of the outline of the pupil region A extracted at the pupil segmenting part 21. The boundary between the pupil region A and the iris region C and the boundary between the pupil region A and the iris granule region B are included in the closed curved line DR1.

The outline portion of the iris granule region B is then extracted from DR1. An elliptical model, for example, can then be applied by utilizing the fact that the outline of the pupil region A is for the most part elliptical. DR1 is not perfectly elliptical but is for the most part elliptical. A coordinate string DR2 for the elliptical shape that most fits DR1 can then be obtained by using a Hough transformation etc. for expanding an ellipse (refer to FIG. 5(b)). When the coordinate string DR2 is obtained, the difference of DR1 and DR2 is then seen as the iris granules and a coordinate string KR1 present at the boundary portion of the pupil region A and the iris granule region B are extracted (FIG. 5(c)). The region surrounded by the coordinate strings KR1 and DR2 is the lower half of the iris granules 5. In this embodiment, as shown in FIG. 3, a description is given taking the example of the case where the iris granules 5 are positioned at the upper part of the pupil 3. However, the region of the iris granules 5 can also be segmented by repeating the process in the case where the iris granules 5 exist, for example, above and below the pupil 3.

Figure 6:
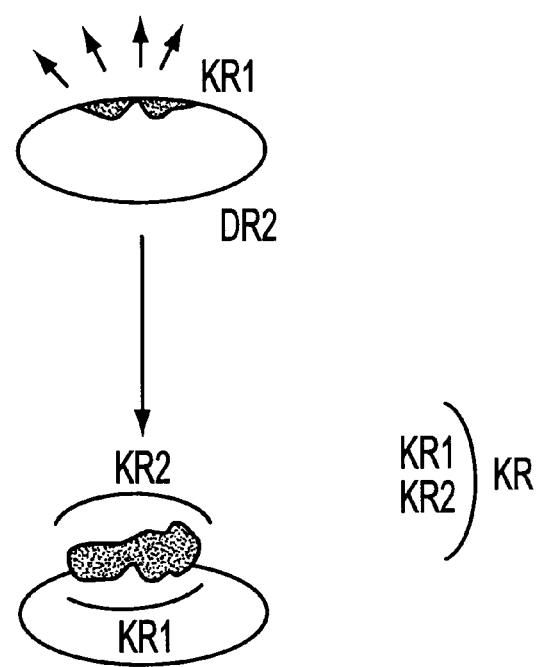
FIG. 6 is a view illustrating a further iris granule region segmenting process.

Next, a method for detecting the region for the upper half of the iris granule region B i.e. the boundary of the iris region C and the iris granule region B is described using FIG. 6. The change in density in a direction towards the outside of the pupil 3 (the direction shown by the small arrows in FIG. 6) is then evaluated from the portion of the outline portion for the lower half of the iris granule region B obtained by the process that includes DR2. Places for which the change in density is greater than a certain threshold value within a pre-defined range are then taken to be the boundary line of the iris region C and the iris granule region B, with this coordinate string then being taken to be the coordinate string KR2 of the boundary portion for the upper half of the iris granule region B. A coordinate string KR, which is the outline KR1 of the lower half and the outline KR2 of the upper half of the iris granule region B combined, then represents the outline of the iris granule region B.

Figure 7:
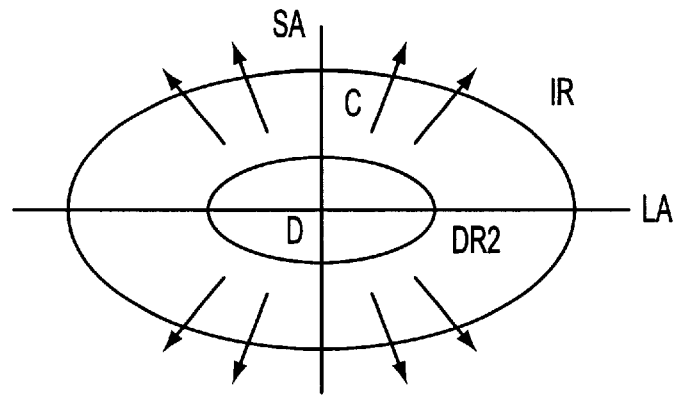
FIG. 7 is a view illustrating an iris region segmenting process.

The outline of the iris region C is extracted at the iris segmenting part 25. Outline lines for the inside of the iris region C forming belt-shaped ellispoids are obtained by processing at the pupil segmenting part 21 and the iris granule segmenting part 22 and the remaining outer outlines are extracted. Portions of changing density are then detected in the same way as for the extracting of the pupil region A. As shown in FIG. 7, the density change portions are evaluated in a direction from the region at the inside of the iris 4 to the outside (the directions shown by the arrows in FIG. 7). When density changes within a pre-defined distance from the pupil region A that are greater than a predefined value are detected, these points are viewed as being in the boundary of the iris region C. An elliptical model is then applied to the obtained coordinate string in the same way as for segmenting of the iris granule region and an ellipse IR fitting the outline of the outside of the iris region C is obtained using, for example, elliptical Hough transformations etc. In this case, the inner ellipse DR2 and the outer ellipse IR are preset so that a source point D, long axis L and short axis SA coincide (but have different degrees of oblateness). The searching range can therefore be limited while the outer ellipse is set.

As a result of the above process, the regions for the iris granules and the iris can be extracted from the image. Next, processing for extracting the characteristics of the iris and the iris granules is carried out.

Figure 8:
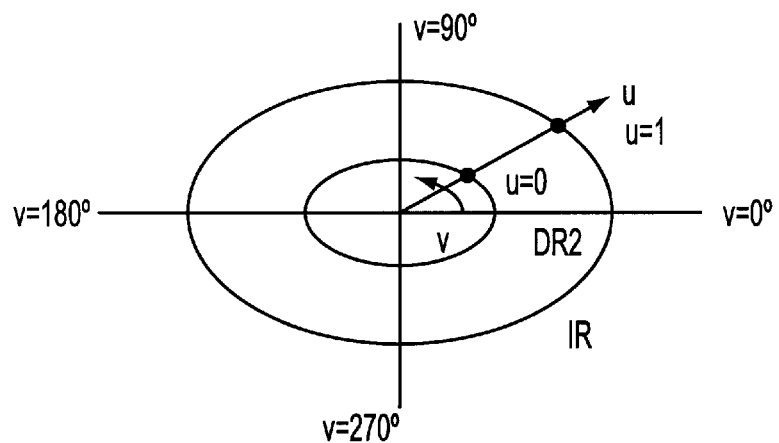
FIG. 8 is a view illustrating an example of settings for a coordinate system for evaluating iris characteristics.

Coordinates for evaluating the characteristics of the extracted iris region C are set at the iris coordinate setting part 26. As shown in FIG. 8, the iris region C has the same source point, long axis and short axis and is viewed as being a region surrounded by the two ellipses having differing degrees of oblateness, i.e. the elliptical-shaped regions expressed by the elliptical coordinate systems u and v. Here, u shows the coordinate in the radial direction and is set to be, for example, 0 on the inner ellipse DR2 and 1 on the outer ellipse IR. Further, v shows the coordinates in the circumferential direction and is set to be 0° and 180° along the long axis and 90° and 270° along the short axis. I.e., the iris region C is expressed in two-dimensional space (u=0 to 1, v=0 to 360°). Because of this, the distribution of characteristics of the iris region C can be evaluated using the consolidated coordinate system (u–v space) even for bodies having differing degrees of oblateness or for cases where the pupil 3 changes (where the size of the pupil 3 changes while an approximately elliptical shape is maintained) for the same body due to changes in the strength of illumination.

The iris region C expressed in two-dimensional space (u–v space) by the iris coordinate setting part 26 is extracted as the characteristic amount peculiar to the body at the iris characteristic extractor 27. The extracted characteristic amount is used as a descriptor based on the texture of the shading of the image and the color distribution etc. For example, the space-frequency distribution of the pattern for the whole of the iris region C or the position, angle or length of the wrinkle walls 4a, the positional relationship of each of the wrinkle walls 4a, the position or length of the dividing ring 4b, or the number, position or size etc. of the hole 4c that are elements that make up the iris region can be used as descriptors. Further, the shape, size and ratio between the inner and outer ellipses for the inner ellipse and outer ellipse for the iris obtained at the iris coordinate setting part 26 can be used as descriptors expressing body differences. The image for the obtained iris region C also changes due to the strength and wavelength used by the light 12, number of lights 12 used and the relative angle of the light 12 and the camera 11. The descriptors obtained from the image while these are being changed can also be used as descriptors peculiar to the body.

Figure 9:
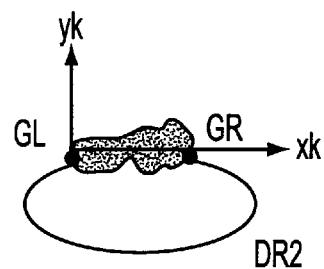
FIG. 9 is a view illustrating an example of settings for a coordinate system for evaluating iris granule characteristics.

Coordinates for evaluating the characteristics of the extracted iris granule region B are set at the iris granule coordinate setting part 23. As shown in FIG. 9, an elliptical coordinate system is used at the iris coordinate setting part 26 in accordance with the elliptical iris region C. At the iris granule coordinate setting part 23, an elliptical coordinate system is not used, with a two-dimensional orthogonal coordinate system (Xk, Yk) being used instead because the shape of the iris granule region B is not elliptical, the characteristics of the elliptical coordinate system are such that the coordinate spacing becomes rapidly narrower as the center of the ellipse is approached and subtle errors in position detection are expressed as large values in an elliptical coordinate system. The axes LA and SA of the ellipse used to express the iris region C, or a line connecting the points of intersection of the ellipse DR2 used to express the outline of the pupil region A and the outline of the pupil granule region B (GL and GR in FIG. 9) and a straight line orthogonal to this line (shown by the axes xk and yk in FIG. 9) can be used a methods for setting the orthogonal coordinate system.

Characteristics peculiar to the body of the iris granule region B expressed by the two-dimensional space coordinates (xk, yk) at the iris granule coordinate setting part 23 are extracted at the iris granule characteristic extractor 24. The extracted characteristics can be used as descriptors based on the texture of the density of the image and the color distribution etc. For example, the size of the iris granule region B, the shape of the outline, and the space-frequency distribution of the pattern for the inner region etc. can be used as descriptors. Further, the image of the iris granule region B obtained can also change due to the strength, number of, and wavelength used by the light 12 and the relative angle of the light 12 and the camera 11. The descriptors obtained from the image during these changes can then be used as descriptors peculiar to the body.

In the above, the characteristic amounts for the iris and the characteristic amounts for the iris granules are extracted and the extracted characteristic amounts are sent to the degree of difference calculator 28 of the body data correlator 14. The degree of difference between the descriptors for the body obtained at the iris characteristic extractor 27 and the iris granule characteristic extractor 24 and the descriptors for the body stored in the body data registry 15 is calculated at the degree of difference calculator 28. In this case, it is appropriate to calculate the degree of difference with all of the body descriptors stored in the body data registry 15. However, the name etc. of the body (horse) currently being photographed and other body information is known already and in cases where only the authenticity of the body information is to be distinguished, just the degree of difference with the applicable body descriptors of the descriptors stored in the body data registry 15 is calculated.

The correlation of the body currently being photographed is identified at the comparator 29 of the body data correlator 14. For example, the name of the corresponding body having the smallest degree of difference within all of the descriptors of the body data registry 15 is outputted to the correlation results output section 16. When the smallest degree of difference is larger than a pre-defined threshold value, results saying that a corresponding body does not exist are outputted. When only the authenticity of the body currently being photographed is to be determined, a judgment can be made as to whether or not the degree of difference is within the range of threshold values.

As described above, animal body identification is carried out by utilizing differences in the irises and iris granules of animals, extracting iris regions and iris granule or granula iridica regions from photographed images of body eyes, setting coordinates for each of the extracted regions and comparing characteristic amounts of each region occurring in a set coordinate system with pre-registered body data. The body identification of the above embodiment can be applied to animals whose irises and iris granules have characteristics peculiar to each body and can also be used with other animals such as, for example, cattle. Further, in the first embodiment, identification was carried out by correlating data for both iris and iris granule characteristics, but carrying out identification by using data for one of either is also possible. The identification accuracy is slightly lower in this case when compared with the case of carrying out identification using data for both but, for example, using only iris data to carry out identification is suitable for application to animals that do not have iris granules or granulae iridica and the scope of application is therefore expanded.

When an eye of a horse is photographed using the camera 11, the head of the horse needs to be fixed to a certain extent, so a special gate is therefore desirable. The camera is then positioned in a specific place (a position from which the eye of the horse can be reliably photographed when the horse enters the gate). The eye is then photographed using the camera 11 with the body of the horse fixed to a certain extent. It is preferable, however, if the eye of one horse is photographed using a number of cameras.

It is also possible for the camera 11 to be separated from the main body of the identifying device 10 and for someone to then photograph the eye of the horse using the camera 11.

In this case, it is not necessary to fix the position of the horse and a fixing gate is therefore not needed. Photographing of the horse can then be made easier as it is now possible to send and receive data in a wireless manner between the camera 11 and the main body of the identifying device 10.

Second Embodiment

Next, a description will be given of a second embodiment of the present invention. This second embodiment relates to a body identifying system applying the body identification technology mentioned in the first embodiment and specifically relates to a racing horse identification management system such as a country-wide racing horse registering system and/or racing horse lineage facilities.

System stability, reliability and usefulness are influenced by the way in which the overall system for registering body data and attribute data for body identification to be described later, saving the body data and attribute data for body identification and having a terminal process for the correlation of the body data in order to obtain and then correlate the iris data and iris granule data present in the racing horse body data is configured. As described in the following, the body identifying system of the present invention does not just carry out identification of horses, but can also carry out registering of body data while maintaining safety as the occasion rises and has the advantage of being able to centrally manage the registered data in one place.

Figure 10:
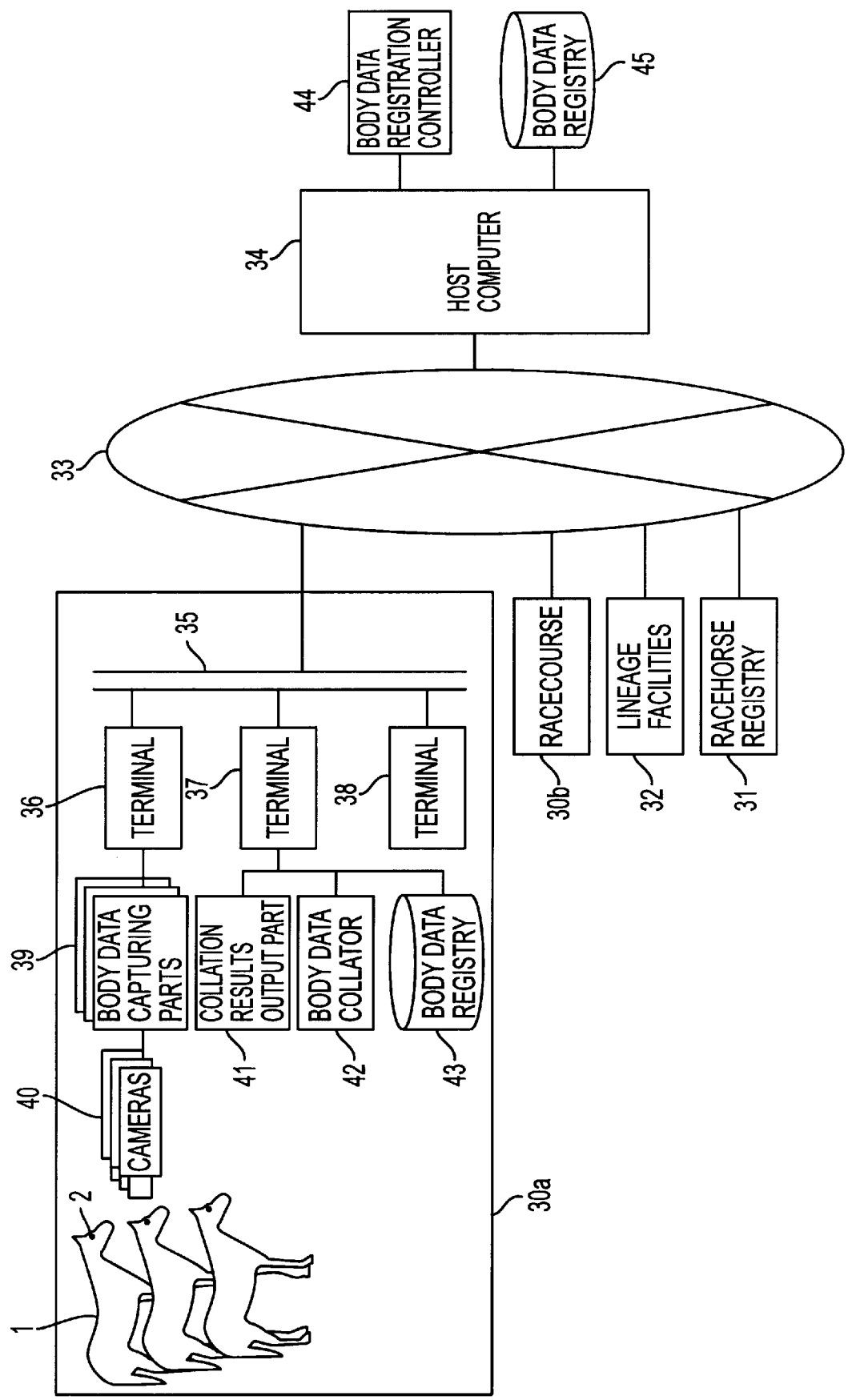
FIG. 10 is a structural view showing a body identification system of a second embodiment.

FIG. 10 is a structural view showing a body identifying system of the second embodiment. In FIG. 10, racecourses 30a and 30b that are spread-out over the whole country, a racehorse registry 31 and a lineage facility 32 are connected to a host computer 34 via a communications line 33. The body identifying systems at the racecourses 30a and 30b, the racehorse registry 31 and the lineage facilities 32 at other racecourses are almost identical but a description is given here taking the example of the body identifying system of the racecourse 30a. The racehorse registry 31 is a registry such as the Japan Racehorse Registry and is for collectively registering and managing racehorses countrywide.

An internal network 35 connected to the communications line 33 is provided at the racecourse 30a, with terminals 36, 37 and 38 being connected to this internal network 35. Body data capturing parts 39 are connected to the terminal 36. A plurality of the body data capturing parts 39 are provided, with these body data capturing parts 39 being connected to cameras 40. The cameras 40 photograph the eyes 2 of the horses 1. Further, a correlation results output part 41, body data correlator 42 and body data registry 43 are connected to the terminal 37. The camera 40, body data capturing parts 39, correlating results output part 41, body data correlator 42 and body data registry 43 have the same functions as in the first embodiment.

On the other hand, a body data registration controller 44 and a body data registry 45 are connected to the host computer 34. The body data registry 45 stores body data i.e. iris data and iris granule or granala iridica data for each of the racehorses registered, as well as storing attribute data for body identification use. This attribute data for body identification is a pedigree registration certificate of the horse name, blood type number, blood record, species, characteristics, address of producer and name of mother and father etc., a unique record number given to the head of the horse, various inspection histories, history of vaccination with preventative injections, medical history and past treatment history drug history, prescription history, image data showing the overall appearance and face of the horse and other newly added data. The attribute data for body identification is data attached to the body data and contains information supplementary to the level and is provisionally registered with the body data. The body data registration controller 44 is a device for registering new body data and attribute data for body identification for the horse at the body data registry 45. The registration and issuance of pedigree registration certificates is currently carried out solely by the Japan Racehorse Registry and it is preferable for the registering of the body data and the attribute data for body identification to the body data registry 45 to be carried out at the same time as the pedigree registration.

The necessary iris data and iris granule data (i.e. the body data) is transferred beforehand from the body data registry 45 connected to the host computer to the body data registry 43 of the racecourse 30a via the communications line 33. Namely, an application file for the body data registry 43 is formed before a race starts at the racecourse. On the actual day of the race at the racecourse, at the paddock, the horses undergo weighing and body identification inspections, etc. The contents of this inspection are mainly a body identification inspection (inspections of facial characteristics and hair color etc.) for specifying whether or not this horse is the actual racehorse listed in the race, in addition to a horseshoe inspection, a horse harness inspection, inspection of a horse number tag surrounding the horses head (race record number) and an overall body inspection, etc. The body identification relating to this embodiment is carried out at the time of this inspection.

The body data correlation relating to this embodiment for the body identification inspection is carried out in the following way. First, the eyes of the racehorses are photographed using the cameras 40 by the inspector covering the paddock and the photographed images are sent to the body data capturing parts 39, where iris data and iris granule data are obtained as the body data in the same way as in the case for the first embodiment. The body data obtained in this way is then sent to the terminal 36, which then sends this data on to a further separate terminal 37 via the internal network 35 while simultaneously sending a collation request to the terminal 36.

The terminal 37 sends the received body data to the body data correlator 42, refers to the body data registry 43 and collates the body data received for the body data correlator 42 and the registered body data, with the correlation results then being outputted to the correlation results output part 41. The output of the correlation results output part 41 can then be sent to, for example, the inspector having the camera 40 to be used with a monitor showing the validity of the correlation. The end of the collation can then be confirmed by the inspector by looking at the monitor and the inspection and body data correlation for the next horse can be gone onto. The camera can then be rapidly pointed in the direction of the eyes of the horse once again and re-photographing can then be performed when it has been determined using the monitor that collation has not been achieved.

Usually, at large scale installations such as racecourses, iris data and iris granule data sent from a plurality of body data capturing parts 39 can be received as input directly at the terminal 36 by having cameras 40 and body data capturing parts 39 operate at a large number of places at the same time in order to capture body data for use in correlation. However, the available processing power is insufficient for the terminal 36 receiving a large amount of body data to perform correlation on a stand-alone basis. In the practical example shown in FIG. 10, the terminal 36 is therefore limited to having functions for communicating with another terminal 37 and for communicating with the host computer 34 via the communications line 33. It is also, of course, possible to provide a plurality of terminals 36 in order to compensate for the lack of processing power.

As described above, according to the second embodiment, simple and accurate racehorse identification can be carried out even by somebody who is not a knowledgeable specialist in matters relating to racehorses in the way that a specialist inspector is. As pluralities of cameras 40 and body data capturing parts 39 are provided, a plurality of racehorses can be identified at the same time.

Third Embodiment

Figure 11:
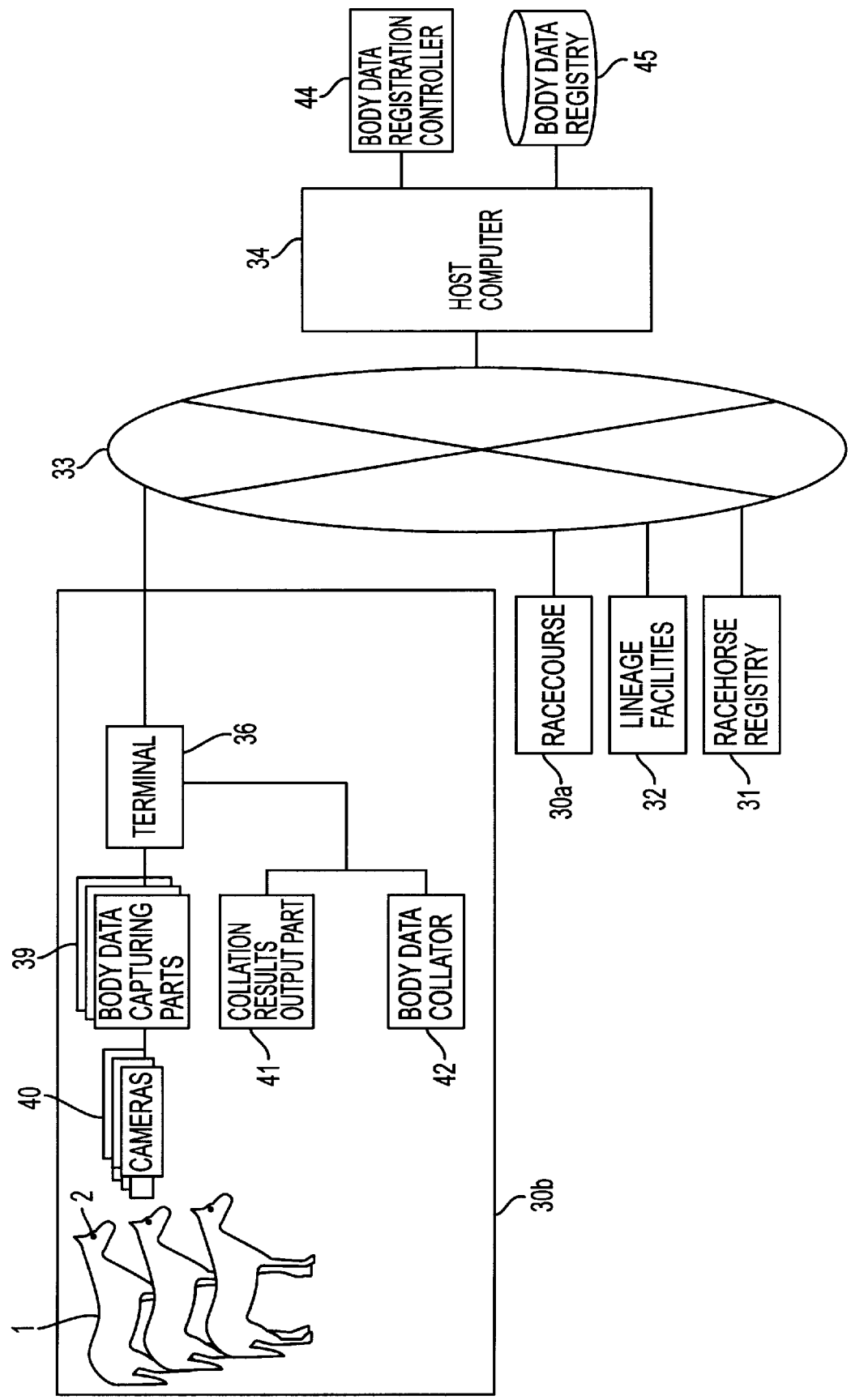
FIG. 11 is a structural view showing a body identification system of a third embodiment.

Next, a third embodiment of the present invention will be described. FIG. 11 is a structural view showing the body identifying system of this third embodiment. The body identifying system of the third embodiment is for centrally managing body data and attribute data for body identification use for racehorses at a host computer.

In FIG. 11, the identification management system for a racecourse 30b is equipped with body data capturing parts 39 that capture data for an image of the eye 2 of the horse 1 photographed by the camera 40 and a terminal 36 that receives the body data as input. The terminal 36 is connected to the host computer 34 via the communications line 33. The body data registry 45 housing attribute data for horse body identification use corresponding to the body data and the body data registration controller 44 for controlling the body data registering process are connected to the host computer 34, with body data and attribute data for body identification use being registered by this body data registration controller 44. Further, the body data collator 42 and the collation results output part 41 are connected to the terminal 36.

When racehorse identification is carried out, a clerk in charge such as the inspector photographs the eye 2 of the horse 1 using the camera 40 and the photographed image is sent to the body data capturing parts 39. Body data is then captured from the image in its original form at the body data capturing parts 39 and the captured body data is sent to the terminal 36. The terminal 36 then sends the body data received as input to the body data correlator 42 and also sends a body data transmission request to the host computer 34. The host computer 34 then sends all of the body data registered at the body data registry 45 to the terminal 36 via the communications line 33 in response to this request.

The body data comprising the iris data and the iris granule or gradula iridica data is, in reality, a small amount of data and can therefore easily be transmitted at high-speed via the communications line 33. The body data received at the terminal 36 is then sequentially transmitted to the body data correlator 42. Body data captured at the body data capturing parts 39 and body data transmitted from the host computer 34 is then correlated using the method at the body data correlator 42, with the correlation results then being outputted from the correlation results output part 41.

According to the third embodiment of the present invention, management efficiency is good because the registered body data can be managed collectively on the host computer side. Further, the calculating load put on the host computer 34 is alleviated because the body data collator 42 is provided on the side of the terminal 36 (on the side of the racecourse 30b). Moreover, the system can be made lightweight when compared with the system of the second embodiment because it is not necessary to provide a body data registering part on the side of the terminal 36.

Fourth Embodiment

Figure 12:
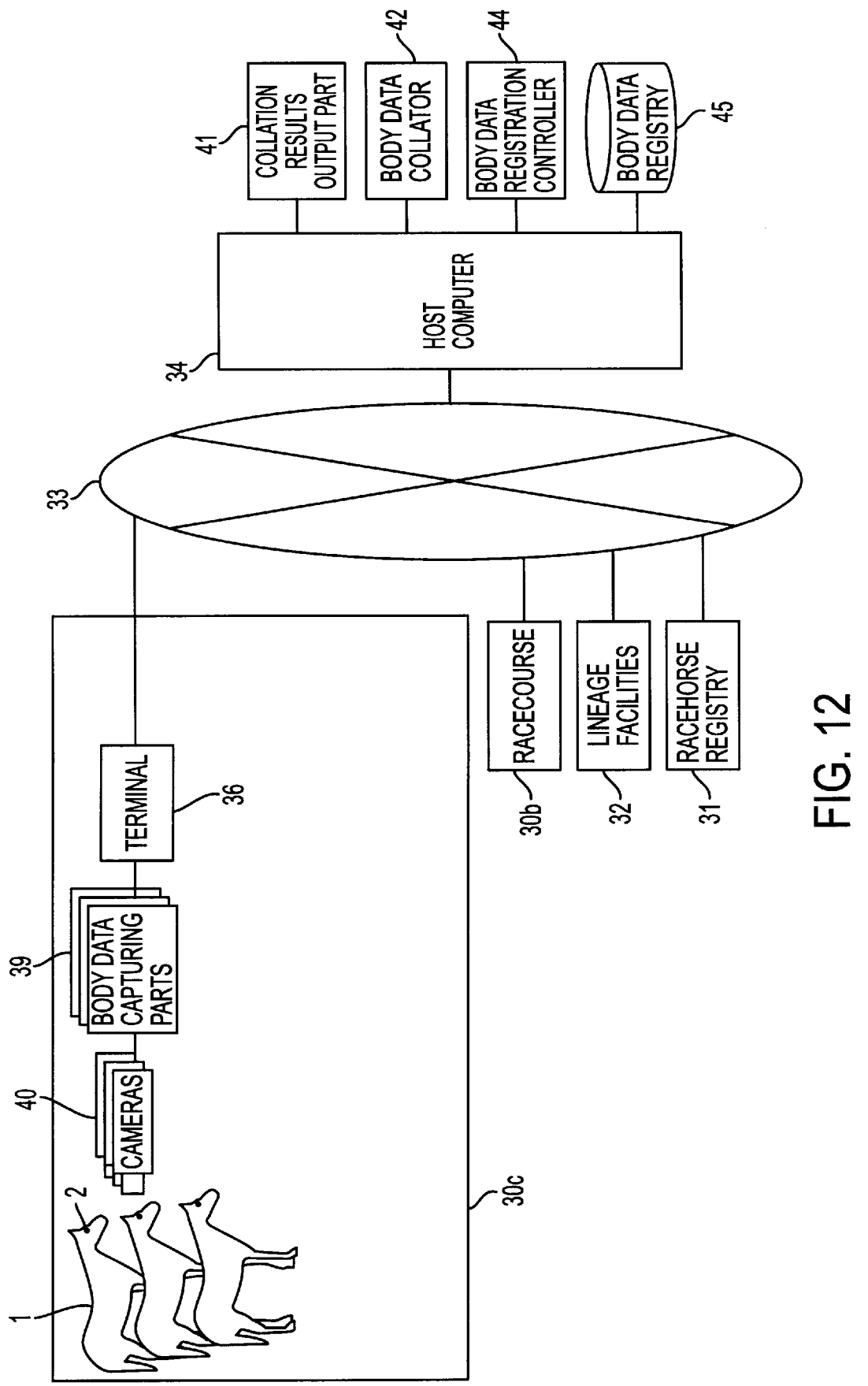
FIG. 12 is a structural view showing a body identification system of a fourth embodiment.

Next, a fourth embodiment of the present invention will be described. FIG. 12 is a structural view showing a body identifying system of the fourth embodiment of the present invention. The characteristics of the body identifying system of the fourth embodiment are that all of the processes from registering to correlating the body data comprising the iris data and the iris granule or granula iridica data are carried out by the host computer. This system is applicable to cases where the processing power of the host computer is large enough to be accessed by racecourses, racehorse registering centers and lineage facilities for each of the racetracks spread countrywide so that all business matters can be processed.

In FIG. 12, the identification management system for a racecourse 30c comprises a plurality of cameras 40, a plurality of body data capturing parts 39 connected to these cameras 40 and a terminal 36 to which the body data capturing parts 39 are connected. The terminal 36 is connected to the host computer 34 via the communications line 33. The body data registration controller 44 and the body data registry 45 are connected to the host computer 34, together with the body data correlator 42 and the correlation results output part 41.

An image of the eye 2 of the horse 1 photographed by the camera 40 is captured at the body data capturing parts 39 so that body data is obtained. The body data is then sent to the terminal 36, and then sent on again from the terminal 36 to the host computer 34 via the communications line 33. Body data is then read-out from the body data registry 45 at the host computer 34 and this body data and the body data sent from the terminal 36 is then collated or compared at the body data correlator 42. Correlation results are then outputted from the correlation results output part 41 and sent to the terminal 36 via the communications line 33. The clerk in charge can then know the correlation results by looking at the correlation results on, for example, a display part of the terminal 36.

As described above, according to the fourth embodiment, the present invention can be made even more lightweight when compared with the third embodiment because body data correlation is also carried out on the side of the host computer rather than just the body data being registered.

Fifth Embodiment

Figure 13:
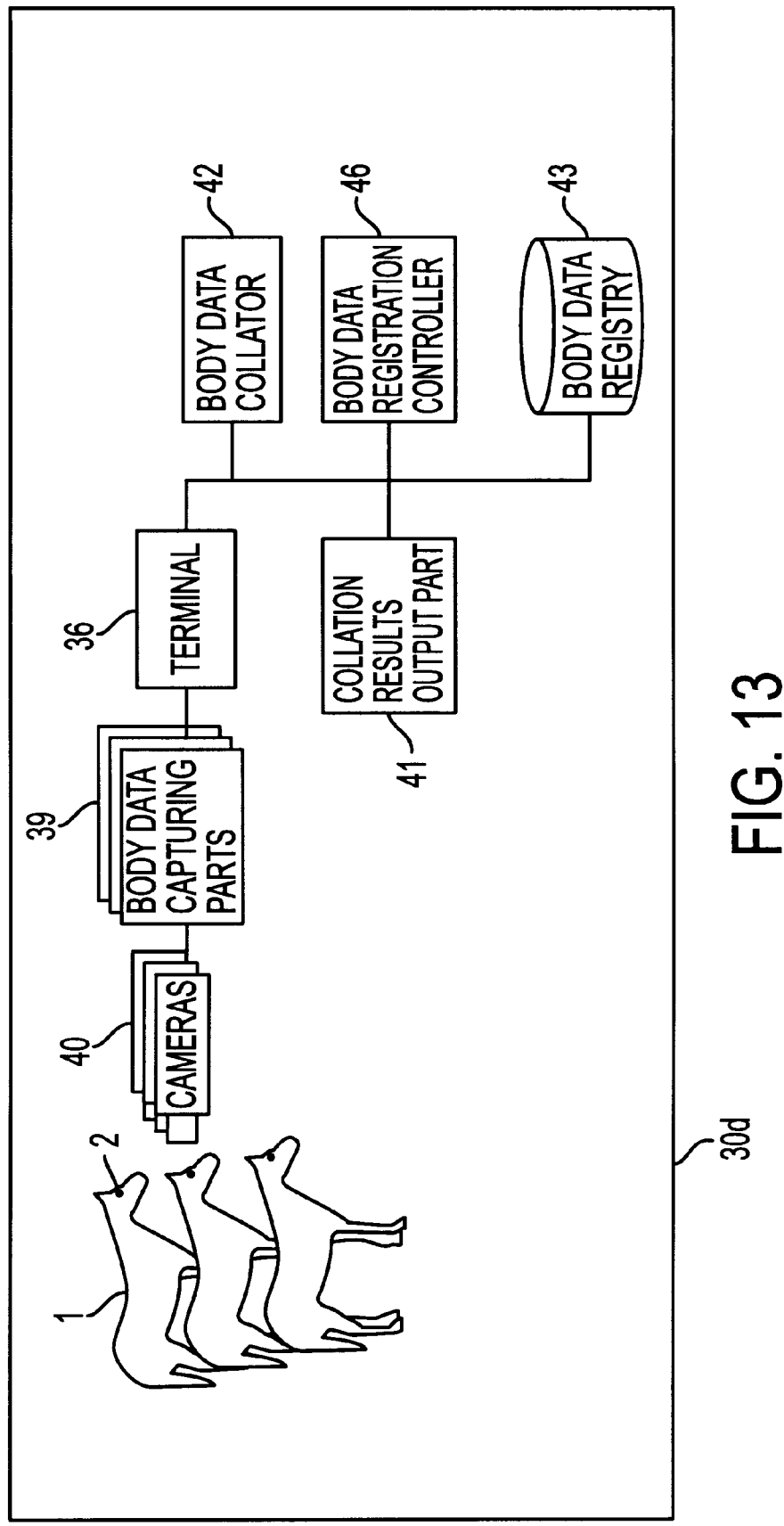
FIG. 13 is a structural view showing a body identification system of a fifth embodiment.

Next, a fifth embodiment of the present invention will be described. FIG. 13 is a structural view showing a body identifying system for a fifth embodiment of the present invention. In the body identifying system of the fifth embodiment a host computer is not connected because body data is registered at the terminal and collation or correlation processing for this body data is also carried out at this terminal.

In FIG. 13, a body identifying system for a racecourse 30d is provided with a plurality of the cameras 40, a plurality of body data capturing parts 39 connected to these cameras 40 and a terminal 36 to which the body data capturing parts 39 are connected. The correlation results output part 41, the body data correlator 42, the body data registry 43 and a body data registration controller 46 are connected to the terminal 36. The body data registry 43 stores the body data in such a manner as to correspond with the attribute data for identification use. Further, the body data registration controller 46 is for controlling the body data registering process.

An image of the eye 2 of the horse 1 photographed using the camera 40 is captured by the body data capturing parts 39 so that body data is obtained. The body data is then sent to the terminal 36, with the terminal 36 then sending this body data on to the body data correlator 42. On the other hand, body data is read from the body data registry 43 and body data collation is carried out at the body data collator 42, with the correlation results then being outputted from the correlation results output part 41.

The system of the fifth embodiment can be constructed, for example, using a personal computer as the terminal 36 and can therefore be utilized by using a comparatively small scale installation.

Sixth Embodiment

Figure 14:
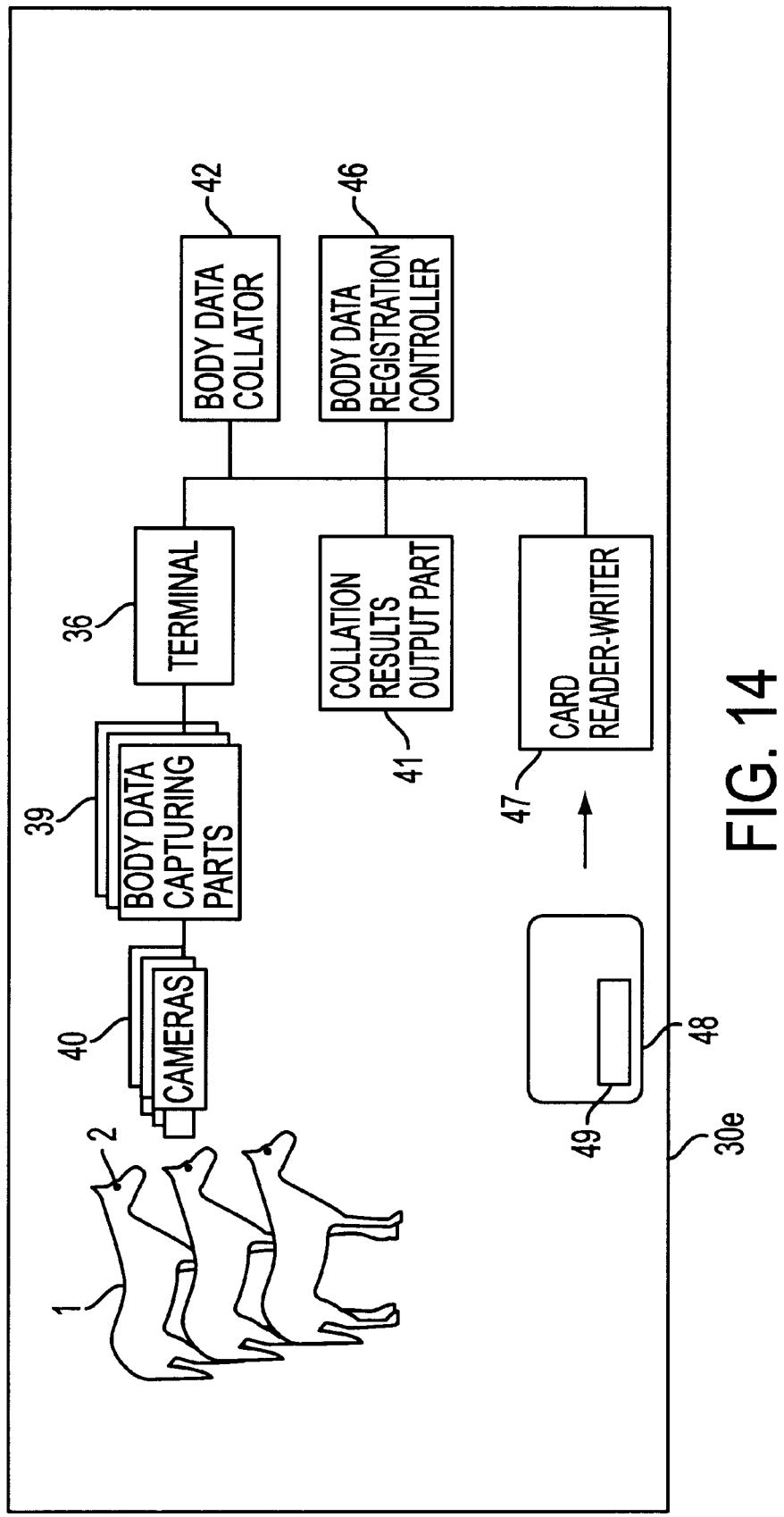
FIG. 14 is a structural view showing a body identification system of a sixth embodiment.

Next, a sixth embodiment of the present invention will be described. FIG. 14 is a structural view showing a body identifying system of a fifth embodiment of the present invention. Body data for racehorses is utilized, for example, at a racecourse by various persons concerned, and this therefore provides a problem with regards to security. The body identifying system for the sixth embodiment is therefore a system where, in order to maintain security of body data, a body data card is registered so that only card owners can carry out identification of the bodies of racehorses.

In FIG. 14, an identification management system for a racecourse 30e is provided with the plurality of cameras 40, the plurality of body data capturing parts 39 connected to these cameras 40, and the terminal 36 to which the body data capturing parts 39 are connected. The correlation results output part 41, body data correlator 42, body data registration controller 46 and a card reader-writer 47 are connected to the terminal 36. The card reader-writer 47 is for reading and writing data to and from a card 48. The body data registration controller 46 controls the processes for registering this data and in particular controls the process for registering the body data. The card 48 comprises a magnetic card or integrated circuit (IC) card and contains a body data registry 49. The body data for the horse and the attribute data for body identification are stored at the body data registry 49. The card 48 is then only possessed by, for example, a specialist registrar who looks-up horses or specific concerned persons.

An image of the eye 2 of the horse 1 photographed by the cameras 40 is captured by the body data capturing parts 39 so that body data is obtained. The body data is then sent to the terminal 36 and then sent on from the terminal 36 to the body data correlator 42. On the other hand, a holder of the card 48 inserts the card 48 into the card reader-writer 47 and the body data stored on the body data registry 49 is read-out, with the read-out body data being sent to the body data correlator 42. The body data obtained at the body data capturing parts 39 and the body data read-out at the card reader-writer 47 is then compared at the body data correlator 42, with the results being outputted from the correlation results output part 41.

Horse body identification can be carried out in the above way but it is preferable if the card 48 can be used at other installations, providing that these are installations constructed from systems making use of the same card reader-writer 47 as the racecourse 30e. It is therefore preferable if the registration and issuance processing of the cards 48 is carried out at a dedicated installation.

As described above, registration and issuance of pedigree registration certificates is carried out at specialist dedicated facilities and it is preferable if the registration of the body data and attribute data for body identification relating to the present invention are registered at the same time as the pedigree registration. In this case, the data has to be registered in such a manner that there is no hacking, falsification, or illegal use of the data. By constructing the systems of the second, third and fourth embodiments, registration of body data is carried out while maintaining security as the occasion calls by utilizing racehorse identification management systems distributed throughout the country, with the registered body data being collectively managed in one place. With the constructions for the fifth and sixth embodiments, body data registered using unique racecourse systems can be collectively managed even with respect to small scale racecourses.

Figure 15:
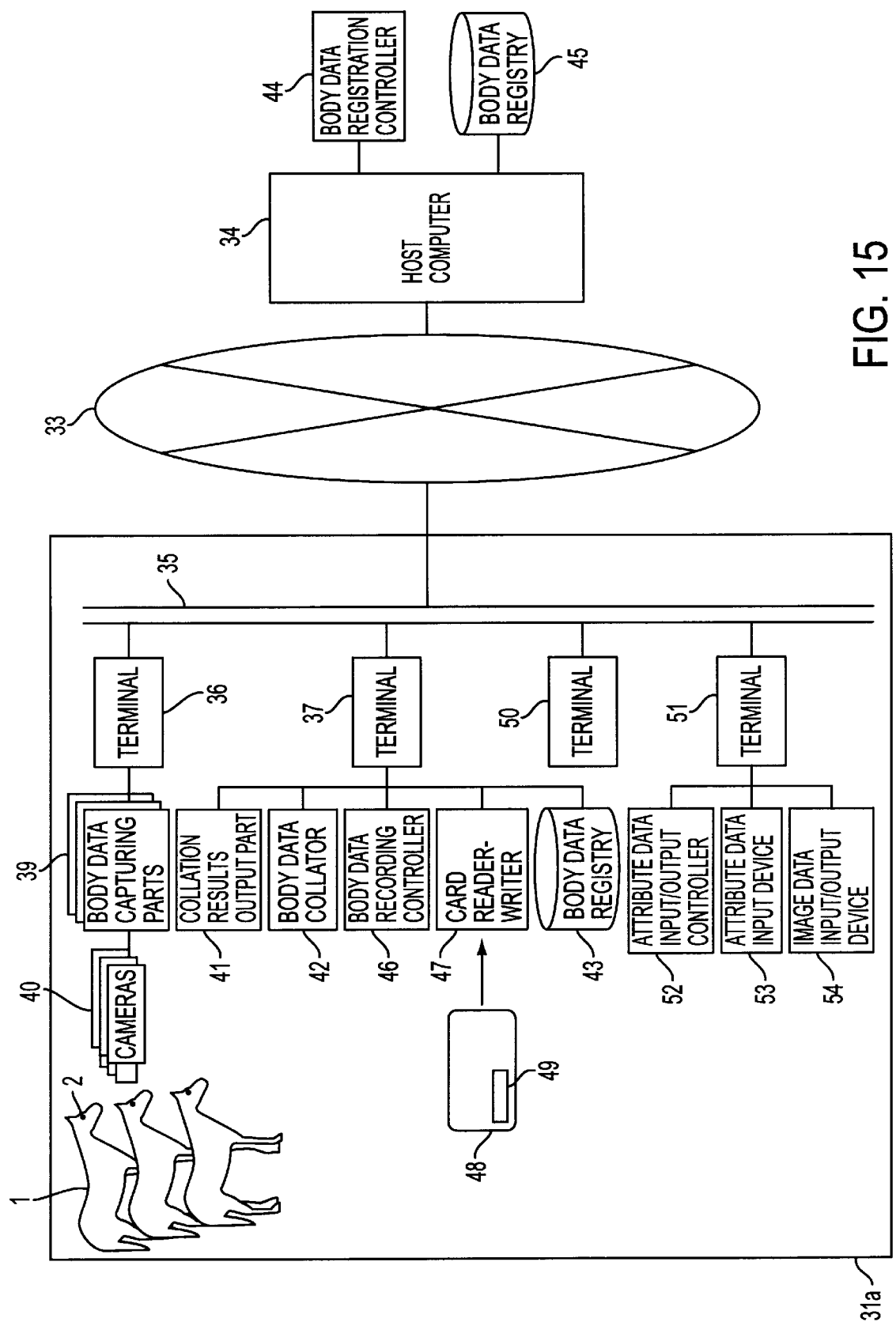
FIG. 15 is a structural view showing a system for registering body data and attribute data for identification use.
Figure 18:
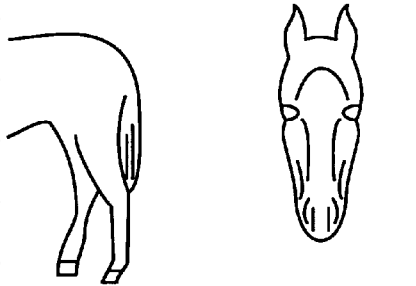
FIG. 18 is a view illustrating attribute data for body identification use included with an image corresponding to body data.
Figure 19:
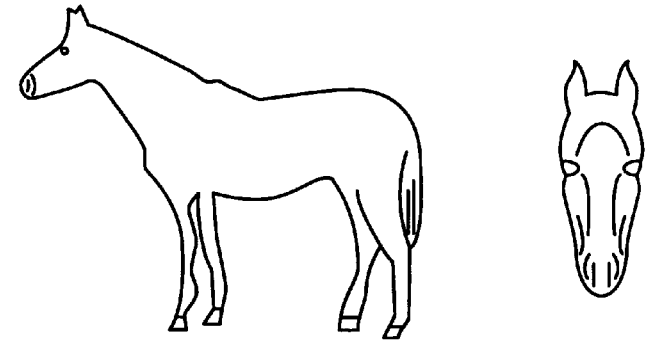
FIG. 19 is a further view illustrating attribute data for body identification use included with an image corresponding to body data.

Next, a description is given of the registration of the body data comprising the iris data and the iris granule or granula iridica data and the attribute data for body identification use. FIG. 15 is a structural view showing a system for registering the body data and the attribute data for identification use. FIG. 16 is a view illustrating the pedigree registration certificate. FIG. 17 is a photograph showing the hair color and characteristics of a horse. FIG. 18 is a view illustrating attribute data included along with the image corresponding to the body data and FIG. 19 is a view illustrating an example of output for attribute data included together with the image corresponding to the body data.

In FIG. 15, the system for registering the body data and the attribute data for body identification use is constructed, for example, at a racehorse registry 31a under the jurisdiction of the Japan Racehorse Registry. Namely, a plurality of cameras 40, a plurality of body data capturing parts 39 connected to the cameras 40 and a terminal 36 to which the body data capturing parts 39 are connected are provided at the racehorse registry 31a. The terminal 36 is then connected to the other terminals 37, 50 and 51 via the internal network 35. The terminals 37, 50 and 51 are then connected to the host computer 34 via the internal network 35 and the communications line 33. The body data registration controller 44 and the body data registry 45 are connected to the host computer 34. The registration of provisionally registered body data inputted from countrywide racehorse management systems and the editing and registering of attribute data for body identification use corresponding to the body data can then be carried out.

The correlation results output part 41, body data correlator 42, body data registration controller 46 and the card reader-writer 47 are connected to the terminal 37. The card reader-writer 47 reads data from and writes data to the card 48. The body data registration controller 46 then controls the registration of this data, i.e. the body data and the attribute data for body identification use. The card 48 comprises a magnetic card or an IC card and contains the body data registry 49. The body data and attribute data for body identification use for the horse is stored at the body data registry 49.

An attribute data input/output controller 52 for controlling the inputting and outputting of attribute data, an attribute data input device 53 for body identification corresponding to body data and an image data input/output device 54 are connected to the terminal 51.

When body data is registered at the racehorse registry 31a, the body data is first captured by the cameras 40 and the body data capturing parts 39, with this body data then being taken as input at the terminal 36. The terminal 36 sends the body data to the host computer 34 via the internal network 35 and the communications line 33. The host computer 34 then provisionally registers the received body data at the body data registry 45 under the control of the body data registration controller 44.

Attribute data for body identification use for the horse to be registered is inputted from the attribute data input device 53 under the control of the attribute data input/output controller 52. As described above, the attribute data for body identification use is the horse's name, blood type number, registration of pedigree, type, characteristics, address of breeder, and mother and father, etc. The inputted attribute data for body identification is then sent to the terminal part 51. The attribute data input device 53 comprises a keyboard device and an optical character reader (OCR). Within the attribute data for body identification, in addition to the contents of the pedigree registration certificate, shown in FIG. 16, there is also various inspection histories, history of vaccination with preventative injections, a medical history and past treatment history, drug history and prescription history. The attribute data for body identification use can therefore be easily inputted using an OCR when a pedigree registration certificate has already been issued. Further, when it is wished to register new data as attribute data for body identification, this data can be inputted using a keyboard, but the inputting method is by no means limited in this respect and attribute data can be inputted using an appropriate input device as necessary.

The characteristics of the horse, such as the characteristics of the head and body and the color of the hair etc. are inputted as attribute data for body identification use via the image data input/output device 54. Specifically, as shown in FIG. 17, a photograph of the whole of or just the head of the horse is read in using, for example, an image sensor, and inputted.

Attribute data for body identification inputted via the attribute data input device 53 and the image data input/output device 54 is sent from the terminal part 51 to the host computer 34 via the internal network 35 and the communications line 33. At the host computer 34, the body data provisionally registered at the body data registry 45 and the attribute data for body identification included with the image transmitted from the terminal part 51 are edited and made to correspond to each other under the control of the body data registration controller 44, as shown in FIG. 18. In order to make this data correspond, the host computer 34 makes the body data and the attribute data correspond and attaches a unique registration number that is given to the horse 1.

The body data comprising the iris data and the iris granule or granula iridica data are made to correspond with the attribute data for body identification, with the host computer 34 then collectively managing both items of data. By carrying out management with the attribute data for body identification having been made to correspond to the body data, the information service provided to concerned persons can be improved because necessary information can be outputted anytime.

FIG. 19 shows an example of the outputting of part of the attribute data for body identification included with the image corresponding to the registered body data, with the body data, registration number and name being outputted together with an image of the whole of and the head of the horse.

In this way, body data registered at the body data registry 45 can be used to identify racehorses at the start of horse races at racecourses. The correlation for identification is as described in each of the embodiments. Here, for example, "corresponds, registration number AS12459876" or "does not correspond" is outputted as the correlation result. When there is a match, the attribute data and the body data shown in FIG. 19 is displayed at the display part of a terminal as necessary. When there is no match, a message such as "iris data not registered" is displayed at the display part of the terminal and the correlation process ends. It is, of course, preferable that the systems for registering body data and attribute data for body identification use are provided at a central registry such as the Japan Racehorse Registry.

In each of the embodiments from the second embodiment onwards described above, body identification can be easily carried out without a special place having to be set aside for animal identification. The work and clerical procedures accompanying animal identification can also be simplified because information relating to animals can now be processed by computer.

What is claimed is:

1. A device for identifying an animal having a granula iridica comprising:

a camera for photographing an eye of an animal and creating an image;

a body data capturer for capturing body data including granula iridica data of the photographed eye from the image created by the camera;

a body data registry for pre-storing a plurality of granula iridica data; and a body data correlator for comparing granula iridica data stored in the body data registry with the captured granula iridica data and identifying the photographed animal as a registered animal or a non-registered animal.

2. An animal body identifying device according to claim 1, wherein the body data further includes iris data.

3. An animal body identifying device according to claim 2, wherein the body data capturer has a segmenting part for segmenting regions of the iris and granulae iridica of the animal's eye and a characteristic extracting part for extracting characteristics of the iris and granula iridica regions segmented at the segmenting part, with the body data register storing characteristics of iris regions and granula iridica regions for a plurality of animals as registered body data.

4. An animal body identifying device according to claim 1, wherein the camera can be separated from a main body of the body identifying device.

5. An animal body identifying system comprising:

a body data capturing device for photographing an eye of an animal and capturing body data including granula iridica data of the animal, said body data capturing device including a segmenting part for segmenting regions of the iris and granula iridica of the animal's eye and a characteristic extracting part for extracting characteristics of the iris and granula iridica regions segmented at the segmenting part; and a body data correlating device, connected to the body data capturing device, for comparing body data obtained from the body data capturing device with pre-registered body data including granula iridica data and determining whether or not the photographed animal is a registered animal.

6. An animal body identifying system according to claim 5, wherein the body data further includes iris data.

7. An animal body identifying system according to claim 5, wherein a plurality of the body data capturing devices are provided.

8. An animal body identifying system according to claim 5, wherein the body data correlating device has a body data registry for storing pre-registered body data and the body data correlating device compares body data obtained from the body data capturing device with body data registered at the body data registry.

9. An animal body identifying system according to claim 8, wherein the body data correlating device has a host device connected to the body data capturing device via a communications line, with the body data registry being provided at the host device.

10. An animal body identifying system according to claim 9, wherein the body data correlating device has a terminal device connected to the body data capturing device and the host device, and the terminal device correlates body data obtained from the body data capturing device and the body data obtained from the body data register.

11. An animal body identifying system according to claim 9, wherein the host device correlates body data obtained from the body data correlating device and body data registered at the body data registry.

12. An animal body identifying system according to claim 10, wherein an input device for inputting attribute data for body identification use is connected to the terminal device, with attribute data for body identification use inputted from the input device being stored at the body data registry.

13. An animal body identifying system according to claim 8, wherein the body data registry is provided at the terminal connected to the body data capturing device.

14. An animal body identifying system according to claim 13, wherein the body data registry can be separated from the terminal device.

* * * * *